United States Patent [19]
Faries, Jr. et al.

[11] Patent Number: 5,862,672
[45] Date of Patent: *Jan. 26, 1999

[54] METHOD AND APPARATUS FOR PROVIDING SUPPLEMENTAL TEMPERATURE CONTROLLED BOTTLES OF STERILE FLUID

[76] Inventors: Durward I. Faries, Jr., 1202 Windrock, McLean, Va. 22102; Bruce R. Heymann, 2700 Hunters Gate Ter., Silver Spring, Md. 20904; Mark Licata, 3208 Forest Hill Ave., Richmond, Va. 23225

[*] Notice: Under 35 U.S.C. 154(b), the term of this patent shall be extended for 567 days.

[21] Appl. No.: 529,477

[22] Filed: Sep. 18, 1995

Related U.S. Application Data

[63] Continuation-in-part of Ser. No. 399,976, Mar. 7, 1995, Pat. No. 5,502,980, which is a continuation-in-part of Ser. No. 274,869, Jul. 14, 1994, Pat. No. 5,400,616, which is a division of Ser. No. 125,279, Sep. 23, 1993, Pat. No. 5,331,820.

[51] Int. Cl.$^6$ .................................................. F25D 11/02
[52] U.S. Cl. .................................................. 62/68; 62/441
[58] Field of Search ............................. 62/342, 68, 440, 62/441

[56] References Cited

U.S. PATENT DOCUMENTS

| | | | |
|---|---|---|---|
| 4,393,659 | 7/1983 | Keyes et al. | 62/66 |
| 4,474,016 | 10/1984 | Winchell | 62/78 |
| 4,522,041 | 6/1985 | Menzel | 62/342 |
| 4,934,152 | 6/1990 | Templeton | 62/66 |
| 5,163,299 | 11/1992 | Faries, Jr. et al. | |
| 5,174,306 | 12/1992 | Marshall . | |
| 5,331,820 | 7/1994 | Faries, Jr. et al. | |
| 5,333,326 | 8/1994 | Faries, Jr. et al. | |
| 5,363,746 | 11/1994 | Gordon | 62/342 |
| 5,400,616 | 3/1995 | Faries, Jr. et al. | |
| 5,402,644 | 4/1995 | Faries, Jr. et al. | |
| 5,429,801 | 7/1995 | Faries, Jr. et al. | |
| 5,457,962 | 10/1995 | Faries, Jr. et al. | |

*Primary Examiner*—William E. Tapolcai

[57] ABSTRACT

Sterile surgical fluid is maintained in one or more temperature controlled basins provided at the top of a cabinet. One or more insulated temperature controlled compartments are formed in the cabinet for storing supplemental supplies of the surgical fluid at the temperatures close to the temperatures of the basins to facilitate replenishing and/or replacing the fluid in the basins. The storage compartments can be used for long-term temperature controlled fluid storage when basin temperature is not being controlled (i.e., between surgical procedures).

10 Claims, 2 Drawing Sheets

METHOD AND APPARATUS FOR PROVIDING SUPPLEMENTAL TEMPERATURE CONTROLLED BOTTLES OF STERILE FLUID

CROSS-REFERENCE TO RELATED APPLICATIONS

This application is a continuation-in-part of our copending U.S. patent application Ser. No. 08/399,976, filed Mar. 7, 1995, now U.S. Pat. No. 5,502,980, which is a continuation-in-part of our U.S. patent application Ser. No. 08/274,869, filed Jul. 14, 1994, now U.S. Pat. No. 5,400,616, which is a division of our U.S. patent application Ser. No. 08/125,279, filed Sep. 23, 1993, now U.S. Pat. No. 5,331,820.

BACKGROUND OF THE INVENTION

1. Technical Field

The present invention pertains to improvements in the method and apparatus for providing sterile surgical saline solution in the operating theater. In particular, the invention simultaneously provides temperature controlled basins for surgical fluid and accessible integral temperature controlled storage for supplemental containers of the required liquid and is an improvement of the methods and apparatus disclosed in U.S. Pat. No. 4,393,659 (Keyes et al), U.S. Pat. No. 4,934,152 (Templeton), U.S. Pat. No. 5,163,299 (Faries, Jr. et al), U.S. Pat. No. 5,331,820 (Faries, Jr. et al), U.S. Pat. No. 5,333,326 (Faries, Jr. et al), U.S. Pat. No. 5,400,616 (Faries, Jr. et al) and the aforesaid U.S. patent application Ser. No. 08/399,976. The entire disclosures in these patents and patent applications are expressly incorporated herein.

2. Discussion of the Prior Art

Some surgical procedures require that an accessible supply of temperature controlled surgical slush be maintained for cooling organs or body parts. In some instances warmed sterile surgical saline is mixed with the slush to produce chilled sterile fluid at selectively controlled temperatures.

A surgical slush producing system having a cabinet with a heat transfer basin at its top is disclosed in U.S. Pat. No. 4,393,659 (Keyes et al). A refrigeration mechanism in the cabinet takes the form of a closed refrigeration loop including: an evaporator in heat exchange relation to the exterior of the heat transfer basin; a compressor; a condenser; and a refrigeration expansion control, all located in the cabinet. A separate product basin is configured to be removably received in the heat transfer basin and separated from the basin by spacers.

During use, the space between the product basin and the heat transfer basin is filled with a liquid such as alcohol or glycol serving as a thermal transfer medium between the two basins. A sterile sheet of material impervious to the thermal transfer medium is disposed between the product basin exterior and the liquid thermal transfer medium to preserve the sterile nature of the product basin. Surgically sterile liquid, such as sodium chloride solution, is placed in the product basin and congeals on the basin side when the refrigeration unit is activated. A scraping tool is used to remove the congealed sterile material to form slush of desired consistency in the basin.

Subsequently, U.S. Pat. No. 4,934,152 (Templeton) disclosed an improved apparatus wherein the product basin function is replaced in favor of a sterilized drape impervious to the sterile surgical liquid, the drape being made to conform to the basin and directly receive the sterile liquid. Congealed liquid is scraped from the conformed drape side to form the desired slush. The Templeton patent also discloses a system having two operating modes. In one mode the basin is cooled to a temperature below the freezing point of the sterile liquid. In the other mode the contents of the basin are heated to a temperature slightly elevated with respect to normal body temperature, typically on the order of 105° F.

In a more recent improvement disclosed in U.S. Pat. No. 5,429,801 (Faries et al), a surgical slush machine is provided with two operating modes, a first mode operating in the range of −10° F. to −70° F. (nominally about −40° F.) for rapidly bringing sterile liquid temperature down to its freezing temperature, and a second mode operating in the range of 20° F. to 40° F. for maintaining the basin near the freezing temperature of the medium.

Placing selectively and individually temperature controlled basins for providing surgical slush and warmed sterile liquid in close adjacency is disclosed in U.S. Pat. No. 5,333,326 (Faries et al). This arrangement allows the surgical staff to adjust the consistency of the sterile slush by the selective addition of warmed sterile solution, and further supports the availability of more than a single sterile compound as is occasionally required in some surgical procedures. What has not heretofore been readily and conveniently available has been an auxiliary supply of bottled sterile compound maintained at appropriate chilled and warmed temperatures for timely replenishment of the contents of the basins. Specifically, it is desirable to pre-chill or pre-warm the stored sterile liquid in order to reduce the time required to achieve desired temperature after the liquid is poured into the drape container. Storing additional bottles in separate warming and cooling units outside the surgical theater necessitates inefficient and time-consuming passage into and out of the operating room by otherwise better occupied medical personnel during the procedure.

OBJECTS AND SUMMARY OF THE INVENTION

It is an object of the present invention to provide a method and apparatus for simultaneously providing basins for maintaining surgical sterile fluid at preselected temperatures and integral temperature controlled storage for bottles of supplemental sterile liquid.

It is another object of the present invention to provide and maintain supplemental supplies of warmed bottled sterile solution for use during surgical procedures.

It is a further object of the present invention to provide and maintain supplemental supplies of chilled bottled sterile solution for use during surgical procedures.

It is an additional object of the present invention to allow replenishment of surgical solution in temperature controlled basins from bottles of solution maintained at similar temperatures in storage cabinets collocated with the basins.

It is yet another object of the present invention to minimize the time and effort required to replace or replenish surgical solution in basins in surgical theaters to improve operating efficiency.

The aforesaid objects can be achieved individually and in combination and it is not intended that the invention be construed as requiring that two or more of said objects be combined.

In accordance with the present invention insulated temperature controlled storage is provided in the basin support cabinet, depending either on independent heating and cooling units or drawing directly from the heating and cooling units provided for basin temperature control. Warmed bottles of sterile surgical solution may be stored in a first storage section and chilled bottles of solution stored in a second storage section, each accessed by optionally transparent doors providing visual indication to operating personnel of supplies on hand.

The above and still further objects, features and advantages of the present invention will become apparent from consideration of the following detailed description of specific embodiments thereof, particularly when taken in conjunction with the accompanying drawings wherein like components are designated by like reference numerals.

DESCRIPTION OF THE PREFERRED EMBODIMENTS

Figure 1:
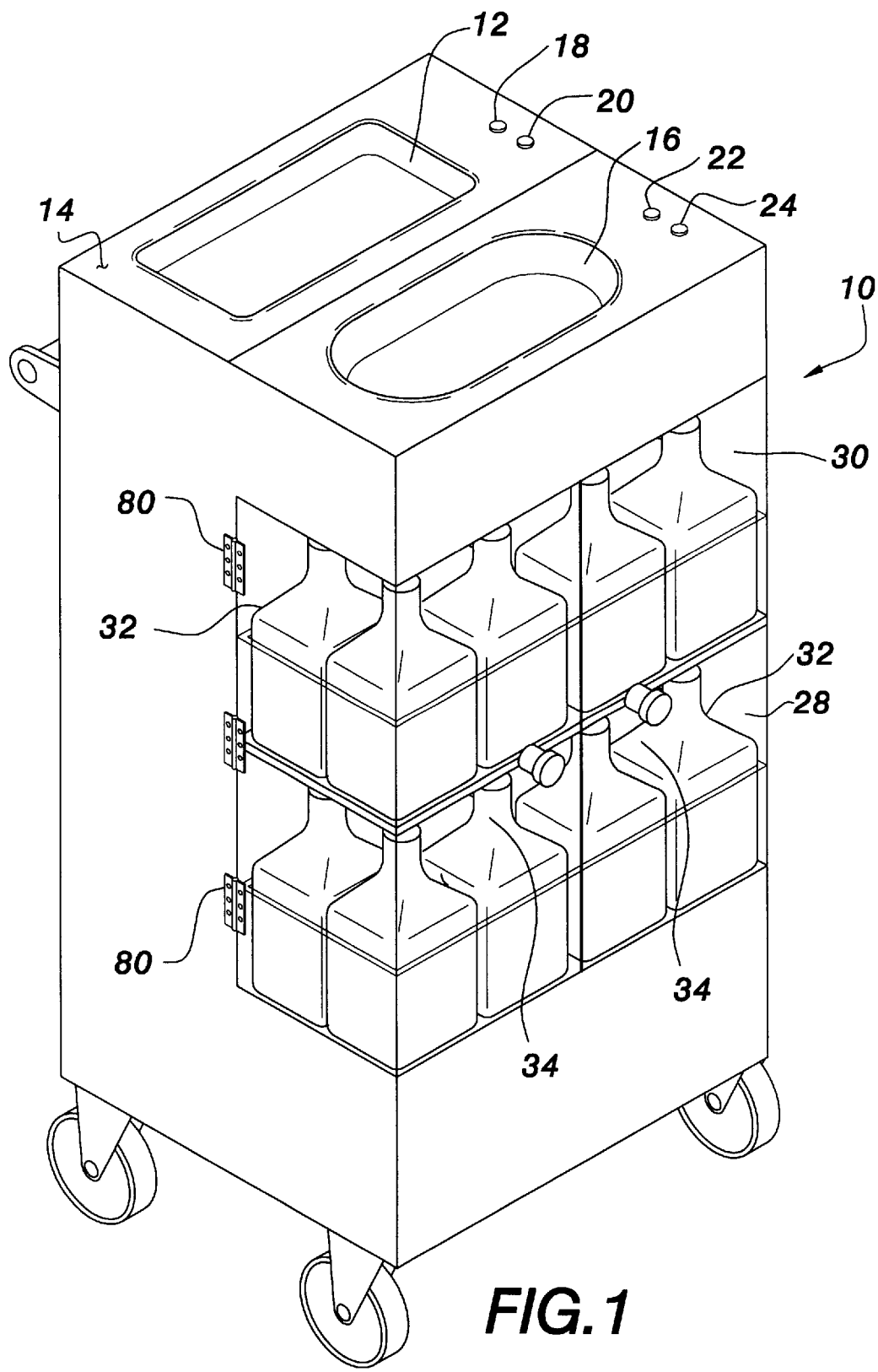
FIG. 1 is a perspective view of a combined surgical slush and warmed sterile liquid cabinet having integral temperature-controlled storage space according to the present invention.

A mobile surgical fluid support cabinet 10 according to the present invention is shown in FIG. 1. A first basin 12 formed in the top surface 14 of cabinet 10 maintains sterile surgical fluid in a chilled slush-like state and a second basin 16 also formed in cabinet top surface 14 maintains a second supply of the same or a different surgical fluid in a warmed state. Disposed on the top surface 14 of cabinet 10 are a cooling unit power switch 18, a cooling unit temperature controller/indicator 20, a heater power switch 22 and a heater unit temperature controller/indicator 24. A sterile drape (not shown), made of a material impervious to the sterile fluids, preferably transparent to allow observation and manipulation of temperature controls therethrough and flexible enough to conform to the concave surface of basins 12 and 16, may be extended over the cabinet top to provide sterile and disposable fluid receptacles within the two basins.

Within cabinet 10, separate temperature-controlled insulated compartments 28 and 30 maintain supplemental sealed bottles 32 of the required fluids in the desired chilled and warmed conditions, respectively, relative to ambient temperature (which in a surgical theater is normally 72° F.). Access to the supplemental bottles 32, or other materials useful in surgical procedures, is through cabinet doors 34, preferably at least partially transparent to allow easy visual monitoring of supplies on hand by operating room personnel. As the supply of surgical fluid in basins 12 and 16 becomes depleted or requires temperature modulation, closed bottles 32 of the appropriate fluid are removed from the cabinet and the contents transferred to the corresponding basin.

Figure 2:
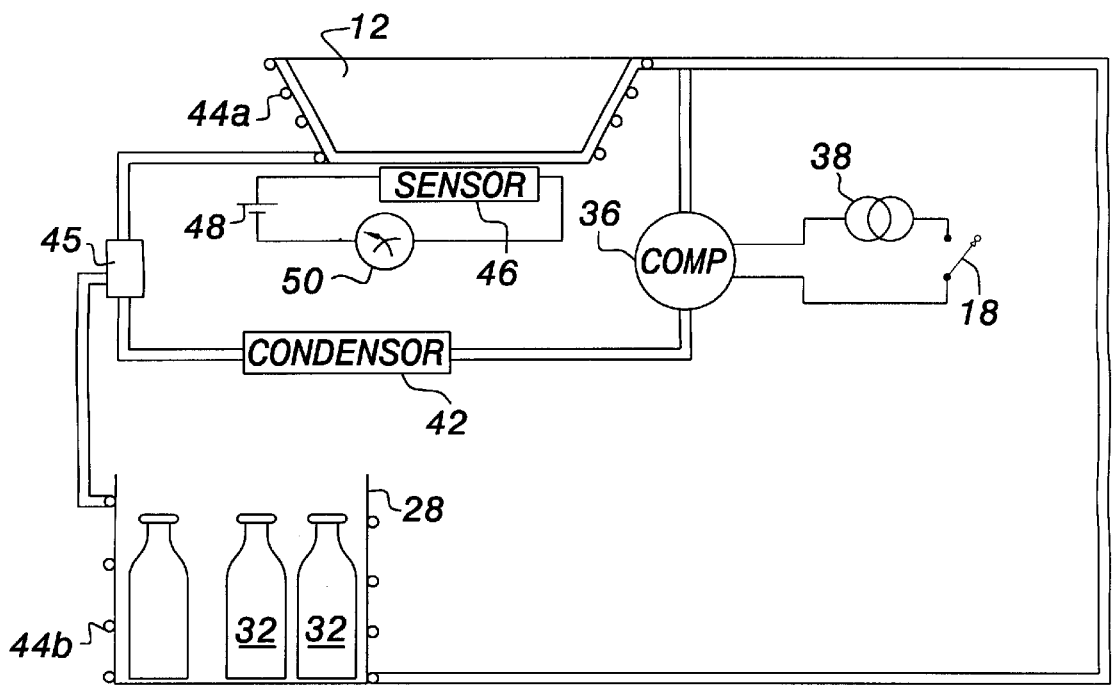
FIG. 2 is an electrical schematic diagram of the cooling system employed by the present invention.

Refrigeration components are illustrated schematically in FIG. 2 including a compressor 36 selectively actuable by means of an electrical power source 38 and an on-off power switch 18. The compressor 36 causes a suitable refrigerant fluid to flow through a series circuit including a condenser 42, one or more evaporator sections 44a and 44b, and a suitable thermal expansion valve 45. A first evaporator portion 44a is disposed about the sides of cooling basin 12 to permit cooling of the basin to a desired temperature, and a second evaporator portion 44b is disposed around chilled or refrigerated compartment 28. A temperature sensor 46 is disposed along the outside surface of the bottom of basin 12 to monitor the temperature of slush formed therein. Sensor 46 is connected in series with a voltage source 48, preferably derived from power source 38, and indicator 50. Indicator 50 measures the current passing through sensor 46 which, in turn, is proportional to the temperature in basin 12. The sensed temperature can then be compared to a predetermined desired temperature and the results of the comparison used to control flow of refrigerant through the evaporators and thus control the basin and storage compartment temperatures, using any number of conventional circuit alternatives. The desired temperature is established by the setting of the controller/indicator 20 on cabinet top 14.

Figure 3:
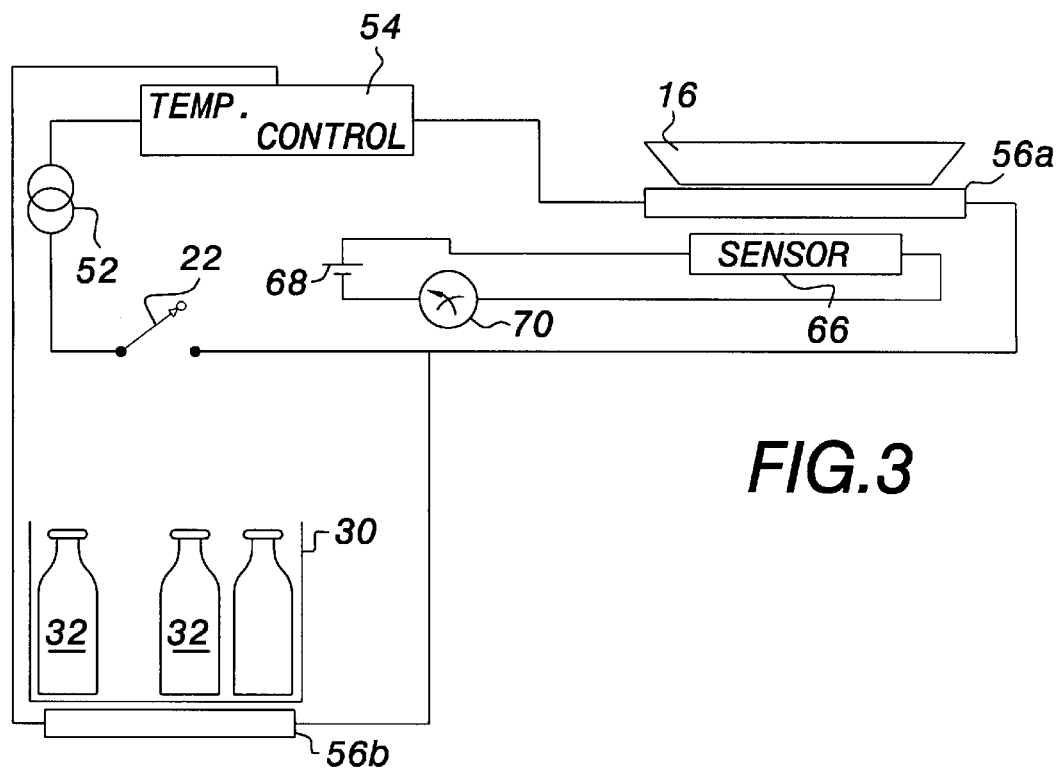
FIG. 3 is an electrical schematic diagram of the heating system employed by the present invention.

Heating components, illustrated schematically in FIG. 3, include a power source 52 connected in series with a temperature control unit 54, a first heater element 56a disposed along the bottom surface of heating basin 16, power control switch 22, and a second heater element 56b disposed in parallel with first heater element 56a and located along the bottom surface of warmed compartment 30. Temperature control unit 54 includes a device for adjusting the current passing through the heating elements 56a and 56b to permit selective adjustment of the heat applied to the liquid in basin 16 and in bottles 32 stored in space 30. The power switch 22 permits selective application and removal of current flow with respect to heaters 56a and 56b.

A temperature sensor 66 is disposed adjacent basin 16 to sense the temperature of the liquid therein. Sensor 66 is connected in series with a voltage source 68 and an indicator 70. Voltage source 68 and power source 52 may be the same source, or the voltage for one may be derived from the other. Indicator 70 measures the current through temperature sensor 66, that current being proportional to the sensed temperature. Indicator 70 and temperature controller 64 may correspond, for example, to the temperature controller/indicator described above.

The temperature maintained in chilled compartment 28 may be controlled and monitored independently with respect to the basin temperature by additional sensors and controllers or, alternatively, independent and separate refrigeration circuits can be provided for the cooling basin 12 and the chilled compartment 28. Similarly independent sensors and controllers can be provided for the warmed compartment of the heating circuit of FIG. 3 or separate independent heating circuits can be supplied for the basin 16 and the warmed storage compartment 30. Moreover, a single heat exchange system similar to, for instance, a heat pump, with thermostatically controlled ductways, can provide appropriate temperature control for both warmed and chilled basins and associated storage compartments. Chilled and warmed compartments 28 and 30, respectively, are maintained at appropriate long-term storage temperatures while basins 12 and 16 are actuated only during periods of surgical activity requiring readily accessible sterile fluids.

Storage access doors 34 shown in FIG. 1 are attached by hinges 80 to the cabinet and formed of insulating yet transparent material, such as glass or lucite, to allow operating room personnel to determine with a glance the inventory of chilled and warmed sterile fluid bottles available to supplement the basins. Storage of warmed bottles is illustrated above the storage of chilled fluid for thermal efficiency but side by side storage or other configurations are contemplated as feasible depending on the available space and the preferences of the operating room personnel. Obviously, the concept of collocated supplemental sterile solution storage of the present invention is equally applicable to single basin cabinets and to cabinets supporting three or more separate fluids and corresponding temperature requirements as it is to the illustrated two-basin example and as well to cabinets designed to accommodate separate product basins rather than a sterile drape arrangement disposed to conform to cabinet top cooling and warming basins.

In use, bottles of the sterile solutions required by a particular surgical procedure are prepared and stored in the appropriate temperature controlled compartments 28 and 30, respectively, prior to commencement of the procedure. The power control switches 18 and 22 are actuated and temperature controller/indicators 20 and 24 are adjusted to achieve and maintain desired chilling and warming temperatures, respectively, in the basins and compartments. The temperature in chilled compartment 28 is maintained between ambient temperature and the freezing temperature of the sterile medium in bottles 32, preferably very close to that freezing temperature, in order to reduce the time required to achieve the desired chilled temperature of the basin when the medium is used. Likewise, the temperature in warmed compartment 30 is maintained between ambient and the regulated heater basin temperature, preferably very close to that basin temperature. Measured amounts of pre-cooled or warmed solution are added to the two basins for ready access by the surgical personnel. As additional solution is required to resupply depleted basins, to quickly adjust solution temperature or to replace contaminated volumes, bottles of solution, observable through the transparent doors 34, are retrieved from the appropriate storage compartment and added to the top surface basin or basins.

Alternatively, the cabinet is kept in a power-on condition with appropriate storage temperatures maintained in chilled and warmed compartments 28 and 30, respectively. Prior to a surgical procedure requiring the sterile solutions, bottles of appropriate fluid are transferred from storage and poured into the basins and the basin heating and cooling systems are actuated to proper temperature.

From the foregoing description, it will be appreciated that the current invention makes available a novel surgical solution system and method for maintaining readily observed and accessed supplemental supplies of prepared fluid at required warmed and chilled temperatures to minimize the time, effort and disruption of operating room procedure.

Having described preferred embodiments of a new and improved method and apparatus for providing supplemental supplies of temperature-conditioned sterile solution, it is believed that other modifications, variations and changes will be suggested to those skilled in the art in view of the teachings set forth herein, it is therefore to be understood that all such variations, modifications and changes are believed to fall within the scope of the present invention as defined by the appended claims.

What is claimed is:

1. In a fluid support cabinet of the type wherein a sterile fluid is maintained at preselected temperature different from ambient temperature in a basin recessed at the cabinet top surface, a method for providing readily accessible supplemental supplies of individual sealed bottles containing thermally pre-treated sterile fluid, said method comprising the steps of:

providing a storage compartment within said cabinet, separate and apart from said basin;

maintaining the temperature in said compartment at a temperature between ambient temperature and said preselected temperature;

providing manual access to said storage compartment;

disposing individual sealed bottles of sterile fluid in said compartment; and selectively manually removing said individual bottles from said compartment and pouring fluid contents from removed bottles into said basin.

2. The method of claim 1 further comprising the step of providing for visual determination of fluid supplies within said compartment through an at least partially transparent cabinet door.

3. The method of claim 1 wherein said basin and storage compartment are selectively cooled to provide chilled sterile fluid.

4. The method of claim 1 wherein said basin and storage compartment are selectively heated to provide warmed sterile fluid.

5. In a fluid support cabinet of the type wherein two sterile fluids are maintained at preselected temperatures in corresponding basins provided at the cabinet top, a method for providing readily accessible supplemental supplies of said sterile fluids maintained at respective preselected temperatures, said method comprising the steps of:

providing two thermally insulated storage compartments within said cabinet;

maintaining each of said storage compartments at a respective controllable temperature between ambient temperature and a respective one of said preselected temperatures;

providing manual access to each of said storage compartments;

disposing containers of said sterile fluids in said storage compartments; and selectively manually removing said containers from said compartment and pouring fluid contents from removed containers into said basins.

6. The method of claim 5 further comprising the step of providing for visual determination of fluid containers within said compartments through transparent cabinet doors.

7. Apparatus for maintaining replenishable supplies of one or more individual sealed bottles containing surgical sterile fluids at preselected temperatures comprising:

a cabinet housing the apparatus;

a basin disposed on said cabinet for receiving surgical sterile fluid;

first temperature control means for selectively and independently establishing the temperature of said fluid in said basin at a predetermined temperature;

a storage compartment formed within said cabinet, separate and thermally insulated from said basin, for storing supplemental supplies of said individual sealed bottles containing sterile fluid;

second temperature control means for controlling the temperature of said storage compartment; and means for accessing said storage compartment to permit manual removal of said sealed bottles from said compartment and pouring of fluid from the removed bottles into said basin.

8. The apparatus of claim 7 wherein said means for accessing said storage compartment comprises a door having a transparent portion to allow visual determination of fluid supplies within said storage compartment.

9. The apparatus of claim 7 wherein said second temperature control means includes means for cooling said storage compartment to a selectively controllable temperature between ambient temperature and said predetermined temperature to provide pre-chilled sterile fluid.

10. The apparatus of claim 7 wherein said second temperature control means includes means for heating said storage compartment to a selectively controllable temperature between ambient temperature and said predetermined temperature to provide pre-warmed sterile fluid.

* * * * *